(12) United States Patent
Diebold

(10) Patent No.: US 6,460,413 B1
(45) Date of Patent: Oct. 8, 2002

(54) IMAGING BASED ON THE ELECTROACOUSTIC EFFECT

(76) Inventor: Gerald J. Diebold, 118 Governor Bradford Dr., Barrington, RI (US) 02806

( * ) Notice: Subject to any disclaimer, the term of this patent is extended or adjusted under 35 U.S.C. 154(b) by 34 days.

(21) Appl. No.: 09/808,833

(22) Filed: Mar. 15, 2001

(51) Int. Cl.$^7$ ................................................ A16B 5/04
(52) U.S. Cl. .......................... 73/584; 73/602; 600/547; 324/600
(58) Field of Search .......................... 73/584, 590, 602; 600/547; 324/600

(56) References Cited

U.S. PATENT DOCUMENTS

| | | | |
|---|---|---|---|
| 3,774,717 A | 11/1973 | Chodorow | 181/0.5 NP |
| 4,407,300 A | * 10/1983 | Davis | 600/547 |
| 4,497,208 A | 2/1985 | Oja et al. | 73/584 |
| 4,552,019 A | 11/1985 | Freeman | 73/584 |
| 5,143,079 A | * 9/1992 | Frei et al. | 600/547 |
| 6,201,990 B1 | * 3/2001 | Wexler et al. | 600/547 |
| 6,403,348 B1 | * 6/2002 | Rubinsky et al. | 435/173.7 |
| 2001/0051774 A1 | * 12/2001 | Littrup et al. | 600/547 |

FOREIGN PATENT DOCUMENTS

| | | | | |
|---|---|---|---|---|
| EP | 0 714 629 A1 | * 6/1996 | | A61B/5/04 |

OTHER PUBLICATIONS

Debye, P., A Method for the Determination of the Mass of Electrolytic Ions, Journal of Chemical Physics, 1, p13 (1933).
Hermans, J., Charged Colloid Particles in an Ultrasonic Field, Philosophical Magazine, 25, p 426, (1938).
Zana and Yeager, Ultrasonic Vibration Potentials, Modern Aspects of Electrochemistry, 14, p1, (1982).
Povey, M.J., Ultrasonic Techniques for Fluid Characterization, p150, (1997).
O'Brien, Electro–Acoustic Effects in a Dilure Suspension of Spherical Particles, Applied Mathematics Preprint, AM86/25.
O'Brien, Cannon and Rowlands, Electroacoustic Determination of Particle Size and Zeta Potential, Journal of Colloid and Interface Science, 173, p406, (1995).
O'Brien, Electro–Acoustic Effects in a Dilure Suspension of Spherical Particles, J. Fluid Mech., 190, p71 (1988).
O'Brien, Electro–Acoustic Equations for a Colloidal Suspension, J. Fluid Mech., 212 p81 (1990).
O'Brien, Electro–Acoustic Reciprocal Relation, Langmuir, 10, p931, (1994).
Beveridge and Diebold, Tissue Imaging Using the Ultrasonic Vibration Potential, Biomedical Optoacoustics, SPIE 3916, 147 (2000).
Matec, Inc., Zeta Potential Determination in Concentrated Colloidal Suspensions, Matec Instruments ESA System.

* cited by examiner

*Primary Examiner*—Hezron Williams
*Assistant Examiner*—Rose M. Miller
(74) *Attorney, Agent, or Firm*—Barlow, Josephs & Holmes, Ltd.

(57) ABSTRACT

The present invention discloses a method and device for imaging based on the electroacoustic effect. The electroacoustic effect takes place when an ultrasonic wave passes through an electrolyte or colloidal suspension. The method and device of the present invention produces images whereby a sound wave is generated at the surface of an object, and, as the wave progresses through the body a voltage is generated in time corresponding to the electroacoustic response of the body at a point in space and time corresponding to the position of the ultrasonic wave in the body. As pulses are launched into the body at different points in space, the signal sensed by an amplifier is used to generate an image.

8 Claims, 3 Drawing Sheets

IMAGING BASED ON THE ELECTROACOUSTIC EFFECT

BACKGROUND OF THE INVENTION

The field of the present invention relates to imaging of bodies, examples being ultrasonic, nuclear magnetic resonance, and x-ray imaging which are used commonly as diagnostic techniques for medicine, non-destructive testing, and quality control in industry.

In 1933, Debye predicted that passage of an ultrasonic wave through a solution of electrolytes would result in the generation of a voltage. The potential generated has become know as the ultrasonic vibration potential. After experimental confirmation of the effect, it was found that colloidal suspensions produced a large signal. The effect is thus also known as the colloidal vibration potential.

The principle of the effect, as well as experimental and theoretical findings have been reviewed by Zana and Yeager, by Povey in his text, and O'Brien, Cannon, and Rowlands. The theory of the electroacoustic effect can be found in these reviews, the references therein, and in the early paper by Hermans. O'Brien and coworkers over the years have developed a detailed theory of the effect; much of his theory can be found in the papers disclosed.

The electroacoustic effect takes place when an ultrasonic wave passes through a fluid containing electrolytes or colloids. In the case of an electrolyte, the different inertias of the ionic species in an electrolyte solution cause them to move to a greater or lesser extent in response to the fluid motion that constitutes a sound wave. The microscopic charge separation that follows from their different dynamic response, when added over the interaction region of the sound wave, results in the macroscopic voltage. Further details can be found in the original paper of Debye. Voltages are also produced when a sound wave passes through a colloidal suspension. Consider the usual case of a colloidal suspension of particles in a fluid where the particles have a higher density than that of the surrounding fluid. Here, the higher mass of a particle relative to that of the fluid volume it displaces means that when an ultrasonic wave passes, the particle motion does not exactly follow the fluid motion, but rather lags it with both a smaller displacement in space and velocity. The different motions of the fluid and particles are described by the equations of fluid dynamics and follows as a result of the higher inertia of a dense particle relative to that of an equivalent volume of the fluid. Colloidal particles are charged bodies with a so-called "zeta" potential, surrounded by a cloud of the opposite charge. The solution thus has overall charge neutrality. The presence of the ultrasonic wave gives rise to a charge separation that arises from distortion of the charge cloud around the particle when the particle fails to move in phase with the fluid. When an ultrasonic wave passes, the fluid carries along the counter charge but the particle and its charge remains more stationary in space. The result of the different motions of the particle and surrounding fluid is that a dipole is generated at the site of each particle, which, when added over a half cycle of an acoustic wave (where the velocity is unidirectional) adds to give a macroscopic voltage, the frequency of the voltage being governed by the frequency of the ultrasonic acoustic wave.

The magnitude of the vibration potential generated in a colloidal suspension, as given by O'Brien, or as summarized in the literature from Matec, Inc., is proportional to the density difference between the particle and the fluid, the volume fraction of the particles, the dynamic mobility, the inverse of the conductivity, and the magnitude of the ultrasonic velocity. Zana and Yeager give somewhat different expressions that involve relaxational parameters, the thickness of the ionic atmosphere, the number density of particles, the particle charge, the dielectric constant, and solvation volume. The magnitude of the signal produced as the ultrasonic wave traverses the body depends on the above quantities; however, the exact details of the theory are not important for the operation of the imaging device described here. Note that in the case of particles with densities lower than that of the fluid, the motion of the particle is opposite to that described above. Again, a voltage is produced, but, for the same relative charge of the particle and fluid, the opposite polarity dipole and overall voltage are produced on each acoustic cycle.

Practical application of the ultrasonic vibration potential to characterization of suspensions has been reported. Freeman describes a device useful in industrial chemical processes for detecting particles or the change in concentration of particles during a chemical process based on the ultrasonic vibration potential. Likewise, Oja, Petersen and Cannon describe a device for characterizing the bulk properties of particulate suspensions using the vibration potential. The Matec Inc. sales literature describes a commercially available device for fluid characterization.

It is to be noted parenthetically that there is another electroacoustic effect that is essentially the reverse of that described above, whereby a voltage is applied to a fluid and an ultrasonic wave is produced. The acoustic wave magnitude is referred to as the "electrokinetic sonic amplitude", as described in the brochure by Matec, Inc. cited above. It is possible to determine colloidal properties of a bulk sample placed in a cell with the device manufactures by Matec that measures the characteristics of sound wave produced following application of a voltage to the cell.

Description of the principle of imaging through the ultrasonic vibration potential has been given by Diebold and Beveridge. An image formed using the ultrasonic vibration potential is thus a map of the response of electroacoustic signal in space, which, in turn, is dependent on the quantities that appear in the theories of the effect as given above. Mixtures of electrolytes and colloidal particles would have a response that is a combination of the responses of the electrolytes and colloidal particles. Whether the body contains electrolytes or colloids alone, or has mixtures, for a given ultrasonic wave of a given frequency and amplitude, there is some voltage response to the wave in fluid. The voltage produced has a magnitude that depends on the ultrasonic wave and the fluid properties. Hereinafter the word colloid will be used for colloids, electrolytes, or mixtures of electrolytes and colloids.

The present document summarizes some of the theoretical aspects of the problem given in the paper by Diebold and Beveridge, and adds new ideas concerning principles and the operation of an actual device. It is to be noted that although the invention uses ultrasonic waves, it is fundamentally different than the well-known method of ultrasonic imaging since the latter records a reflected wave as the means of imaging while the invention described here records a voltage produced by the object itself in response to the ultrasonic waves.

It is therefore an object of the present invention to provide a means for formation of an image of a body. Imaging is carried out for the same diagnostic purposes as in x-ray imaging, NMR imaging, ultrasound imaging, or photoacoustic imaging, namely, for visualizing the inside of bodies.

Such information is useful for diagnostic purposes, as in medicine and nondestructive testing.

It is also an object of the present invention to provide a means of image formation based on a different principle, namely, the electroacoustic effect, which will have properties unique to the method, in particular contrast, based on a completely new principle for imaging, namely, the ultrasonic vibration potential.

SUMMARY OF THE INVENTION

Consider a one-dimensional response, which in the case of a colloidal suspension, would be a concentration of the suspension that varies as a function of distance from the launching point of an ultrasonic wave. Take a 10 cm thick layer with the launching point of the ultrasonic wave at x=0, and with non-colloidal "inert" fluid extending throughout the 10 cm region except between points 3 and 5 cm from the origin where a colloidal suspension is found. The region between 3 and 5 cm will be referred to as the active region. Electrodes are placed at the points x=0 and x=10 cm where the voltage is recorded. It is assumed that the body is a weak conductor of electricity and that the voltage generated at its endpoints can be sensed with a high input impedance amplifier. The pulsed ultrasonic wave in this example is considered as having a wavelength much smaller than 1 cm; say 0.1 mm, and a pulse width of a duration that corresponds to 1 mm, so that about ten cycles are in the pulse. On launching the ultrasonic wave no signal is produced until the first half cycle of the wave reaches the 3 cm point, enters the colloid, and produces a uni-polar voltage. When the second half cycle of the wave reaches the interface, it begins to generate a voltage of the opposite polarity, subtracting from that generated by the first part of the wave. The process repeats itself as subsequent cycles of the ultrasonic wave enter the active region containing the colloid giving an alternating voltage at the electrodes. Further, for the simple case presented here, it can be seen that the output voltage is proportional to the integral of the acoustic velocity in the pulse from the point x=3 to the point x=5. When the pulse is totally inside the active region, the integral of the pulse velocity is zero and no voltage is produced between the points x=3 and 5, and of course, x=0 and 10 where the electrodes are placed. Next, the pulse begins to exit the active region. As the pulse reaches x=5 cm, the part of the pulse immediately extending outside the active region gives no signal, but the part remaining in the active region produces a voltage. The result is that an overall voltage is again recorded with the electrodes. An alternating voltage is produced again as the pulse moves in space until all of the acoustic pulse exits the active region. When the pulse is wholly in the region x>5, no voltage is produced. When the magnitude of the ac voltage signal versus time data are plotted as Voltage (magnitude) versus Z (distance), a plot such as shown in FIG. 2 would be generated. The active region between Z=3 cm and Z=5 cm, where the vibration potential is generated, can be seen on the plot as defined by the peaks at these two points.

It can be seen that a recording of the voltage gives a profile of the colloid spatial distribution within the body, in this case the size of the ac voltage indicating that the pulse is entering or leaving the active region containing colloid. Knowledge of the sound speed permits transformation of the voltage vs. time profile into a colloid "response" vs. distance profile. Of course response involves all of the factors given by theory. Such a profile can locate objects within a body. When sharp boundaries are not present between the colloid and its inert surroundings, description of the voltage production must include the concept of a "response gradient", which would describe the gradient of the colloid concentration in space. The details of the voltage generation process can be described as proportional to the integral of the response gradient of the medium with the ultrasonic pulse. Note that plots of signal vs. distance in the sample can be given meaning through empirical methods by correlating the features of plots with known features in control samples. A detailed knowledge of the theory of signal production is not essential for obtaining useful information.

Simple examples of the use of the device would be for determining the location of blood or blood vessels within the human body, or the presence of colloidal fluids in opaque, weakly conducting objects. Chodorow has shown that blood can be detected through use of the ultrasonic vibration potential. In the case of blood veins, for instance, the voltage response of the electroacoustic imaging device would be greater for the blood vein than for muscle or fatty tissue since the blood contains both electrolytes and cells that are colloidal in nature. Thus, a large contrast in the image would be expected at the site of blood or lymph in proximity to tissue with a low fluid content. A possible application of the imaging method would be in detecting the dimensions of arteries and veins, and the early detection of tumors, which are known to have increased vascularization. With regard to living tissue, the device would be to a certain extent a blood detector. From the standpoint of nondestructive testing, the presence of a fluid in a within solid or porous material would be detectable since the solid cannot produce a substantial electroacoustic effect, but the fluid can.

BRIEF DESCRIPTION OF THE DRAWINGS

The novel features which are characteristic of the present invention are set forth in the appended claims. However, the invention's preferred embodiments, together with further objects and attendant advantages, will be best understood by reference to the following detailed description taken in connection with the accompanying drawings in which:

DETAILED DESCRIPTION OF THE PREFERRED EMBODIMENT

The present invention comprises an ultrasonic transducer that is driven by a pulse generator, electrodes for picking up the voltage generated by the ultrasonic vibration potential at the surface of the body, a receiver that detects the minute voltage produced, a means of moving the transducer along the surface of the body, and a recording device. In the simplest version of the device the voltage is displayed on an oscilloscope as signal vs. time, which can be converted into signal vs. distance through knowledge of the sound speed. In a second embodiment of the device, the transducer is scanned in two dimensions along the surface of the body as voltage vs. time data is collected. A device such as a computer converts the signal at each point in the XY scan with the Z amplitude dependence into a three-dimensional image.

Figure 1:
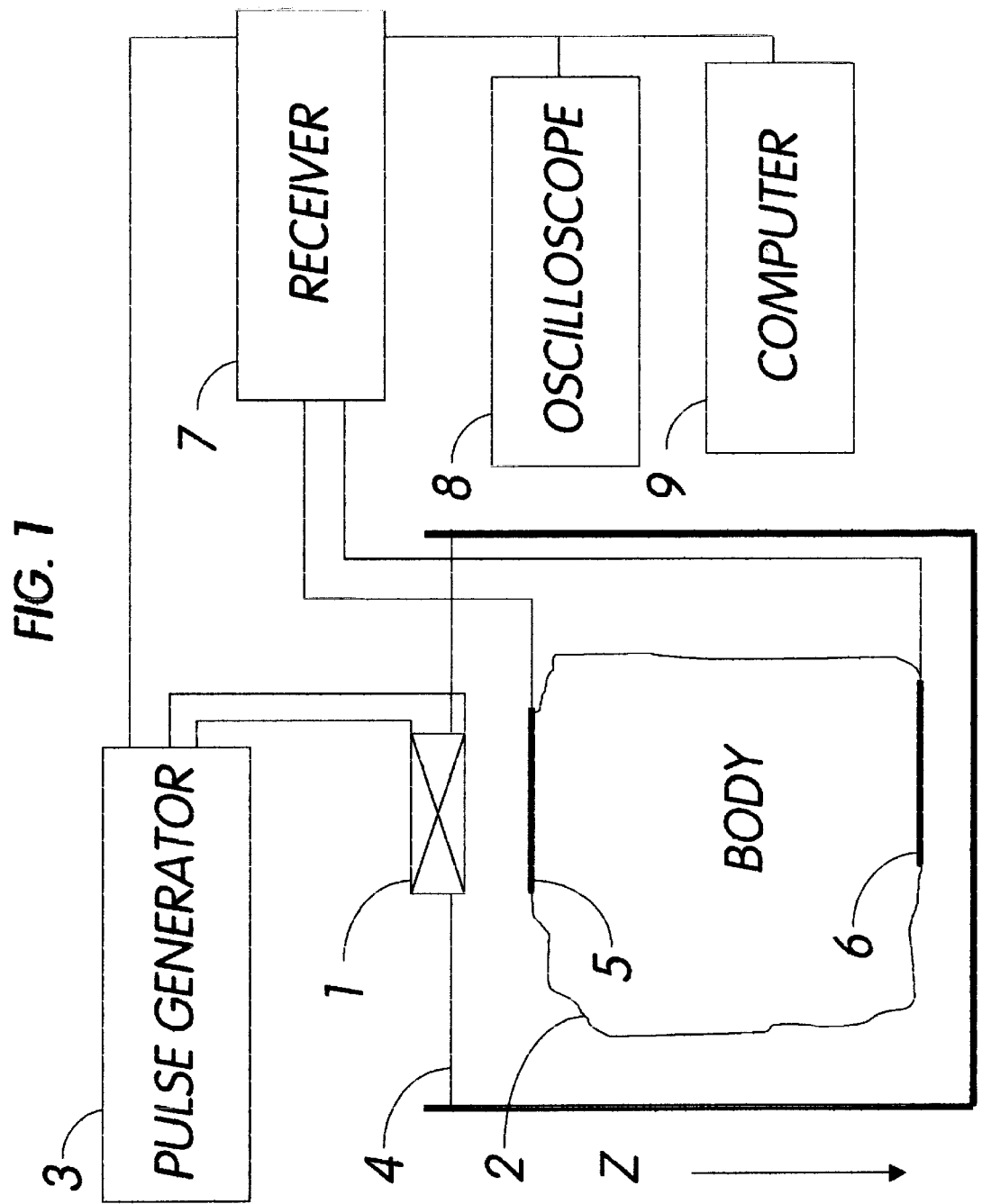
FIG. 1 is a schematic diagram of the device of the present invention.

Turning first to FIG. 1, the present invention is shown. A voltage vs. time signal is generated by placing a transducer 1, such as a conventional PZT (lead zirconate titanate) or PVDF (polyvinylidene fluoride) transducer, in contact with the object 2 and exciting the transducer 1 with an electrical pulse by means of a conventional ultrasonic pulse generator 3. The transducer 1 can be of a geometry such that it focuses the ultrasonic radiation inside the object 2 under investigation. The frequency at which the transducer 1 is driven depends on the characteristics of the colloid within the body 2 under investigation. Generally a frequency is chosen so that the wave produces the largest signal and can traverse the body 2 under investigation without severe attenuation and at the same time gives the best resolution. Several factors determine the optimal frequency, but frequencies in the kilohertz or megahertz range are expected to be the most useful since such frequencies are commonly used in generation of the ultrasonic vibration potential.

An acoustic delay line 4 can be placed between the transducer 1 and the body 2 that transmits the ultrasound to the body 2 thus giving a time delay in the production of the signal. Electrodes 5,6 are attached to the body 2 and the voltage generated is sent to a sensitive receiver 7 operating at the same frequency as the ultrasonic transducer 1. The electrodes 5,6 are required to transmit the signal from the body 2 under study to wires or cables that are fed to the input of the receiver 7. The electrodes 5,6 can be conducting films, plates, or foils applied to the surface of the body 2 whose functioning may be enhanced by the use of conducting pastes or liquids. The signal generator 3 can produce a burst of ac voltage, or it can produce a voltage spike. The function of the electrical signal is that it drives the transducer 1 to give an ultrasonic burst that is transmitted into the body. The received signal from the burst would be an ac signal of the same frequency of the pulse generator 3. The magnitude of the ac signal can be detected giving the magnitude of the ac signal and passed on as its output. The output of the receiver 7 recording the ac signal is fed to an oscilloscope 8 or other equivalent device to produce a plot of voltage vs. time, which corresponds to voltage versus distance in the body. For purposes of viewing, the amplitude of the signal would typically be "detected" giving a dc voltage proportional to the magnitude of the ac signal. Through use of a computer 9 to store the signal from the receiver 7, this device would produce a one-dimensional picture of the body, that can be called an "alpha" scan where signal vs. depth is determined. The depth can be assigned the Z coordinate.

Figure 2:
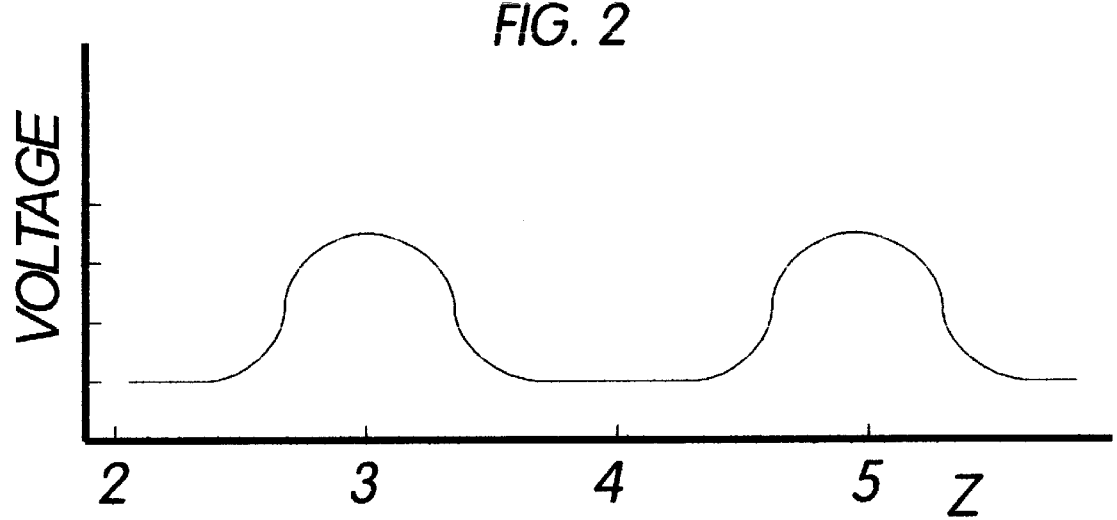
FIG. 2 is a graph of the output generated by the device of the present invention.

The signal-to-noise ratio in the signal from the receiver 7 can be improved by a standard processing method known as time, or signal averaging, where signals from successive pulses are added in the computer 9 at each point in time. The signal adds coherently with that from previous pulses; the noise, on the other hand, adds incoherently, averaging to zero in the long time limit. FIG. 2 shows what might be a typical signal from a hypothetical body with symmetry on one dimension, as described in the first paragraph of the Summary of the Invention.

Figure 3:
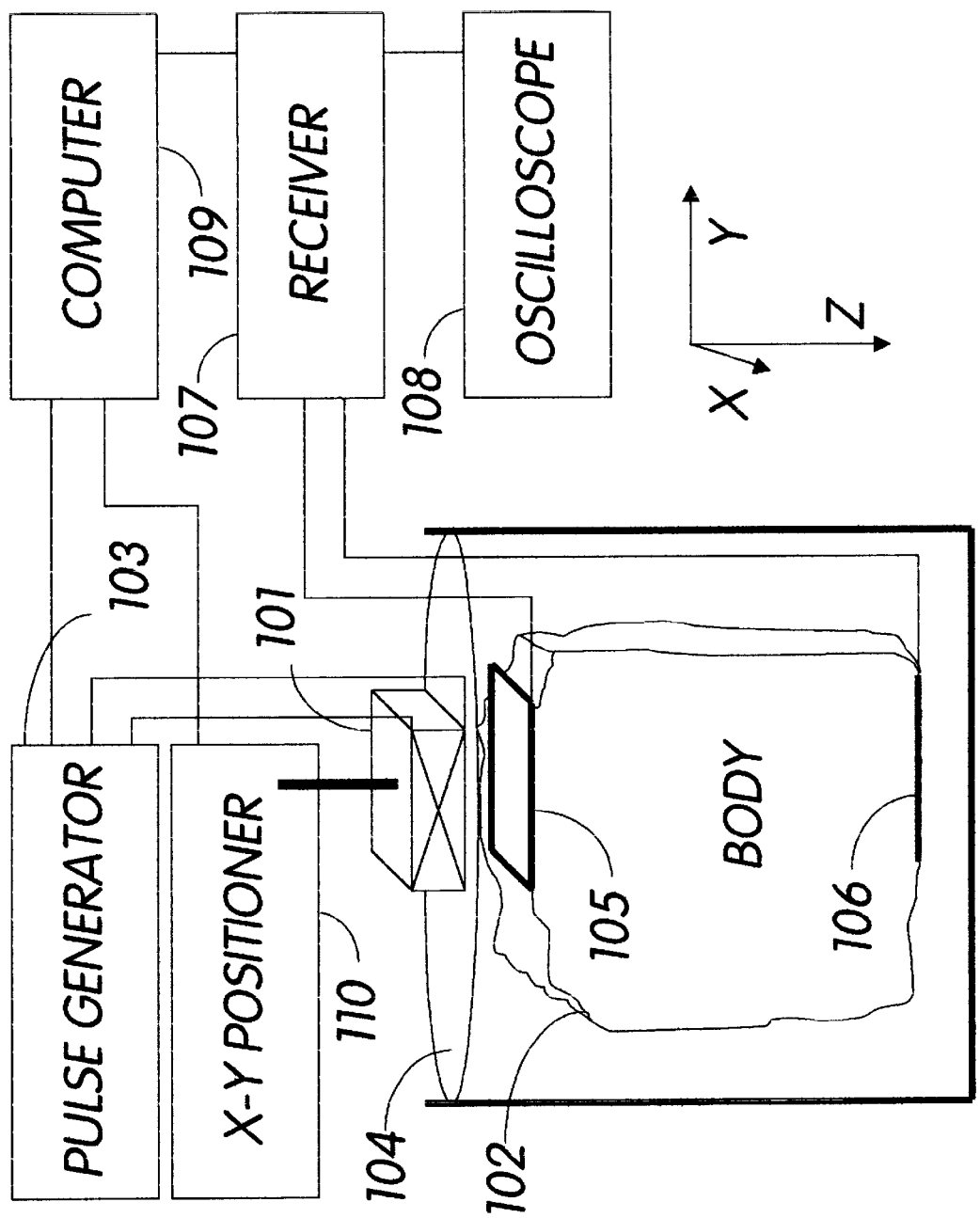
FIG. 3 is a schematic diagram of an alternative embodiment of the device of the present invention.

Turning to FIG. 3, a second embodiment of the present invention is shown, the transducer and electronics are the same, but the transducer 101 is scanned in two other dimensions, X and Y, to make a plot of the voltage vs. time at various positions of the transducer 101 along the X and Y directions. Such a scan can be referred to as a "beta" scan. The only modification of the instrument in FIG. 1 is to add a two-dimensional scanning device 110 that moves the transducer 101 in two directions along the surface of the body 102. Again, a data acquisition instrument such as a computer 109 with appropriate inputs for taking data from both the receiver 107 and scanner 110. The data acquisition device 109 is used to store data and to plot the signal magnitude as a function of the coordinates. It is possible to carry out the same scanning of the body 102 by using composite transducers that scan the ultrasound inside the body using conventional phased array techniques. The method of scanning the ultrasound is not important, only that the ultrasonic radiation be moved in space across or around the object to probe different parts of the body 102 while the signal is acquired as a function of space inside the body 102. The signal acquired by moving the ultrasound within the body 102 permits a three dimensional image of the voltage produced at coordinates X, Y, and Z to be formed, recalling that the Z coordinate is equivalent to the time after launching the pulse. In one embodiment of the invention, color would indicate the magnitude of the signal.

The exact method of scanning or geometry of scanning is variable. The transducer 101 can be rotated around the body 102 and signals acquired at different angles. Such rotation is facilitated by the use of a coupling agent (not shown) that permits the ultrasound to pass into the body 102 so that the transducer 101 is not in direct contact with the body 102 of interest. Such signals can be used to construct an image of the body 102 through computer reconstruction algorithms, again using the position of the transducer 101 and the signal versus time information.

Different frequencies can be used in forming the image so that different images are acquired at different frequencies. Such different images can be subtracted giving a contrast based on the frequency dependence of the vibration potential. In practice, driving PZT at overtones can give the higher frequencies so that the transducer would not have to be changed in forming an image based on an overtone of the original frequency.

It would be appreciated by those skilled in the art that various changes and modifications can be made to the illustrated embodiments without departing from the spirit of the present invention. All such modifications and changes are intended to be covered by the appended claims.

What is claimed:

1. A method of creating an image of a body comprising:
   generating an ultrasonic vibration;
   directing said ultrasonic vibration into a body to be imaged, thereby generating an ultrasonic vibration potential within said body;
   measuring said ultrasonic vibration potential; and
   processing said ultrasonic vibration potential measurement to generate an image of said body.

2. The method of creating an image of a body in claim 1, wherein said steps of generating an ultrasonic vibration and directing said ultrasonic vibration further comprises, generating and directing said ultrasonic vibration using an ultrasonic transducer device.

3. The method of creating an image of a body in claim 1, wherein said step of measuring said ultrasonic vibration potential comprises, measuring the magnitude of said ultrasonic vibration potential using electrodes placed adjacent to said body to be imaged.

4. A method of creating an image of a body comprising:
   generating an ultrasonic vibration;
   directing said ultrasonic vibration into a body to be imaged at a controlled location, thereby generating an ultrasonic vibration potential within said body;
   measuring the magnitude of said ultrasonic vibration potential;
   repeating said steps of generating said ultrasonic vibration, directing said ultrasonic vibration and measuring said ultrasonic vibration potential at a plurality of controlled locations, thereby generating an ultrasonic vibration potential measurement for each controlled location; and processing said ultrasonic vibration potential measurement from each of said controlled locations to generate an image of said body.

5. An apparatus for creating an image of a body comprising:

a device for generating and directing an ultrasonic vibration into a body to be imaged at a controlled location, thereby generating an ultrasonic vibration potential within said body;

a device for measuring the magnitude of said ultrasonic vibration potential; and a device for processing said magnitude measurement of said vibration potential to generate an image of said body.

6. The apparatus for creating an image of a body of claim 5 wherein, said device for generating and directing an ultrasonic vibration is an ultrasonic transducer.

7. The apparatus for creating an image of a body of claim 6 wherein, said ultrasonic transducer can be controllably directed to a plurality of points within said body to be imaged.

8. The apparatus for creating an image of a body of claim 5 wherein, said device for measuring the magnitude of said ultrasonic vibration potential comprises at least one electrode.

* * * * *